United States Patent
Sump et al.

(10) Patent No.: US 6,872,227 B2
(45) Date of Patent: Mar. 29, 2005

(54) STRIP-LIKE IMPLANT

(75) Inventors: Raimo Sump, Hamburg (DE); Christoph Walther, Dorfstr. (DE)

(73) Assignee: Ethicon GmbH (DE)

(*) Notice: Subject to any disclaimer, the term of this patent is extended or adjusted under 35 U.S.C. 154(b) by 0 days.

(21) Appl. No.: 10/169,326

(22) PCT Filed: Dec. 11, 2000

(86) PCT No.: PCT/EP00/12491
§ 371 (c)(1),
(2), (4) Date: Jun. 27, 2002

(87) PCT Pub. No.: WO01/49095
PCT Pub. Date: Jul. 12, 2001

(65) Prior Publication Data
US 2003/0004580 A1 Jan. 2, 2003

(30) Foreign Application Priority Data
Dec. 29, 1999 (DE) .......................................... 199 64 081

(51) Int. Cl.[7] ............................. A61F 2/08; A61B 17/08
(52) U.S. Cl. ....................................... 623/13.2; 606/151
(58) Field of Search ............................ 623/13.2, 13.11, 623/23.72, 13.19; 606/151–154, 213; 602/42, 44

(56) References Cited

U.S. PATENT DOCUMENTS

| 3,513,484 A | * | 5/1970 | Hausner .................. 523/13.11 |
| 3,545,008 A | * | 12/1970 | Bader, Jr. ................ 623/13.15 |
| 4,455,690 A | * | 6/1984 | Homsy .................... 623/13.15 |
| 5,197,983 A | * | 3/1993 | Berman et al. ............. 623/13.2 |
| 5,368,602 A | | 11/1994 | de la Torre |
| 5,441,508 A | * | 8/1995 | Gazielly et al. ............. 606/151 |
| 5,584,884 A | * | 12/1996 | Pignataro ........................ 623/8 |
| 5,788,625 A | * | 8/1998 | Plouhar et al. ................ 600/36 |
| 5,922,026 A | | 7/1999 | Chin |
| 5,968,051 A | * | 10/1999 | Luckman et al. ............. 606/88 |
| 5,997,565 A | | 12/1999 | Inoue |
| 2002/0019635 A1 | * | 2/2002 | Wenstrom et al. ............ 606/72 |
| 2002/0019670 A1 | * | 2/2002 | Crawley et al. ......... 623/11.11 |
| 2002/0169464 A1 | * | 11/2002 | Latour ........................ 606/151 |
| 2003/0191480 A1 | * | 10/2003 | Ulmsten et al. ............ 606/151 |

* cited by examiner

Primary Examiner—Alvin Stewart

(57) ABSTRACT

A strip-like implant (1) has a tape (2) with a first end (4) and with a second end (6). In the area of at least one of the two ends (4, 6), a disk-like application aid (10) aligned with the plane of the tape (2) is arranged. The disk-like application aid can also be constructed in the shape of two jaws of a surgical gripping instrument which is set up to grip an implant tape.

7 Claims, 3 Drawing Sheets

STRIP-LIKE IMPLANT

RELATED CASE

This application claims the benefit of international application serial number PCT/EP00/12491 filed on Dec. 11, 2000.

BACKGROUND OF THE INVENTION

The invention relates to a strip-like implant which has a tape with a first end and with a second end, as well as a surgical gripping instrument with two jaws, which is set up to grip an implant tape.

Strip-like implants, e.g. in the form of resorbable or non-resorbable meshes or gauze strips (tapes), are used e.g. to support or bind tissue. When such an implant is to be used in a surgical operation, it is often necessary to guide one end area or both end areas of the implant through tissue. For this, a large area of tissue must usually be prepared, and after the implant has been applied and positioned, the usually not inconsiderable wound in the end area of the implant must be closed. This is time-consuming and stressful for the patient.

The object of the invention is to provide a possibility for guiding a strip-like implant quickly and gently through tissue.

BRIEF SUMMARY OF THE INVENTION

This object is achieved by a strip-like implant with the features of claim 1 as well as by a surgical gripping instrument with the features of claim 9. Advantageous versions of the invention are given in the dependent claims.

The basic concept of the invention is a disk-like application aid with which a strip-like implant (implant tape) can be pulled through tissue. The disk-like application aid is arranged either in the area of one of the ends of the implant tape (claim 1) or constructed as jaws of a surgical instrument (claim 9), both of which have the same effect.

The strip-like implant according to the invention has a tape with a first end and with a second end. A disk-like application aid aligned with the plane of the tape is arranged in the area of at least one of the two ends.

The disk-like application aid reinforces the end area of the tape and thus enables the tape to be pulled through tissue with the help of a gripping instrument. In the process, the application aid provides the tissue quickly and gently with an opening which is no larger than is absolutely necessary for pulling through the tape. Thus an extensive tissue preparation is dispensed with. With the help of the application aid, only the area of tissue which is also actually required to position the strip-like implant is prepared. The specific placing of the implant is guaranteed by means of the application aid as required by the surgeon. In particular, the implant can lie flat without difficulty, if it is to lie uniformly flat. Similarly, if desired, the implant can also be inserted twisted. Through the disk-like application aid which is aligned with the plane of the tape (i.e. runs essentially parallel to the plane of the tape), the end area of the tape is thus constructed so that the implant can be pulled through the desired tissue or lengthwise between two layers of tissue without major problems. Almost automatically, tissue is prepared only for the area that is required for the implant.

All resorbable or non-resorbable materials suitable for the medical field can be considered as material for the tape. Mixtures of resorbable and non-resorbable materials are also conceivable. For the disk-like application aid, non-resorbable materials such as metals, plastics and ceramics are particularly suitable; in principle, however, resorbable materials can also be used.

Application areas are e.g. the augmentation of tendon sutures or the strength support in the case of abdominal wall defects.

Preferably, the maximum width of the application aid measured perpendicular to the longitudinal axis of the tape is at least as great as the width of the tape in the area of the application aid. With this version, the opening required for pulling the tape through tissue can be wholly created by means of the application aid without the edges of the tape cutting into the opening.

Numerous designs are conceivable for the application aid. For one version, the application aid is designed as a one-piece disk which is attached to one side of the tape. In another version, the application aid is designed as a double disk, both parts of which are attached to opposite sides of the tape and enclose the tape between them. The application aid, that is e.g. the one-piece disk or both parts of the double disk, can be attached to the tape using clips or adhesive. Depending on the material, it is also conceivable to weld the application aid to the end area of the tape. Another possibility is to pour the material for the application aid, e.g. a melted plastic or a plastic which has not yet been cured, round the end area of the tape and in doing so fully shape the application aid. Similarly, the end area of the tape can be reinforced by melting on the application aid.

Preferably, the application aid is circular, elliptical, oval or rhombic in the plane of the tape, but other forms are also possible. In a particularly preferred version, the application aid is a double disk with two round halves of the same size, the diameter of which is greater than the width of the tape, the end area of the tape being arranged between the two halves.

The application aid can have an atraumatically designed edge and/or a cutting edge. It can be achieved by the design of the edges of the application aid that, when the implant is pulled through tissue, the application aid cuts the tissue gently only where it is absolutely necessary.

The disk-like application aid can achieve the same effect if it is not integrated into a strip-like implant but rather forms a part of a surgical gripping instrument which serves for pulling through a conventional strip-like implant. Such a surgical gripping instrument has two jaws and is set up to grip an implant tape. The two jaws are designed as a disk-like application aid aligned to the plane of the tape when gripping the tape.

Preferably, the two jaws are each designed as small disks between which the tape can be gripped. When the end area of a conventional mesh strip or implant tape is clamped between the two jaws of the surgical gripping instrument according to the invention, the same effect is achieved as when the disk-like application aid of a strip-like implant according to the invention is gripped with a conventional forceps-like operating instrument. When the operating instrument according to the invention is used, the opening in the tissue required for pulling through the implant tape is created by the two jaws.

To prevent the end area of an implant tape gripped by the surgical gripping instrument from slipping out of the jaws, preferably, clamping means project from at least one of the two jaws, directed towards the other jaw. These can be e.g. one or more spikes or teeth, interlocking teeth or a corrugation.

Preferably, at least one of the two jaws is circular, elliptical, oval or rhombic in the plane of the tape. In a preferred design, the two jaws have the same outline. The surgical gripping instrument is advantageously used with implant tapes the width of which is at most as great as the dimension of the jaws in the direction of the width of the implant tape.

In the same way as the application aid of the strip-like implant according to the invention preferably has an atraumatically designed edge and/or a cutting edge, in the surgical gripping instrument according to the invention preferably at least one of the two jaws has an atraumatically designed edge and/or a cutting edge.

BRIEF DESCRIPTION OF THE SEVERAL VIEWS OF THE DRAWINGS

In the following, the invention is explained in more detail using embodiments. The Figures show in FIG. 1 in parts (a) to (e) top views of the undersides of different versions of strip-like implants according to the invention (in partial view), FIG. 2 in parts (a) to (c) side views of various versions of strip-like implants according to the invention (in partial view), which are constructed as in FIG. 1, FIG. 3 in parts (a) to (e) top views of further versions of strip-like implants according to the invention (in partial view), FIG. 4 in parts (a) to (c) side views of various versions of strip-like implants according to the invention (in partial view) which are constructed as in FIG. 3, and FIG. 5 a perspective view of a surgical gripping instrument according to the invention, in part (a) with opened jaws and in part (b) with closed jaws when gripping an implant tape.

DETAILED DESCRIPTION OF THE INVENTION

Figure 1:
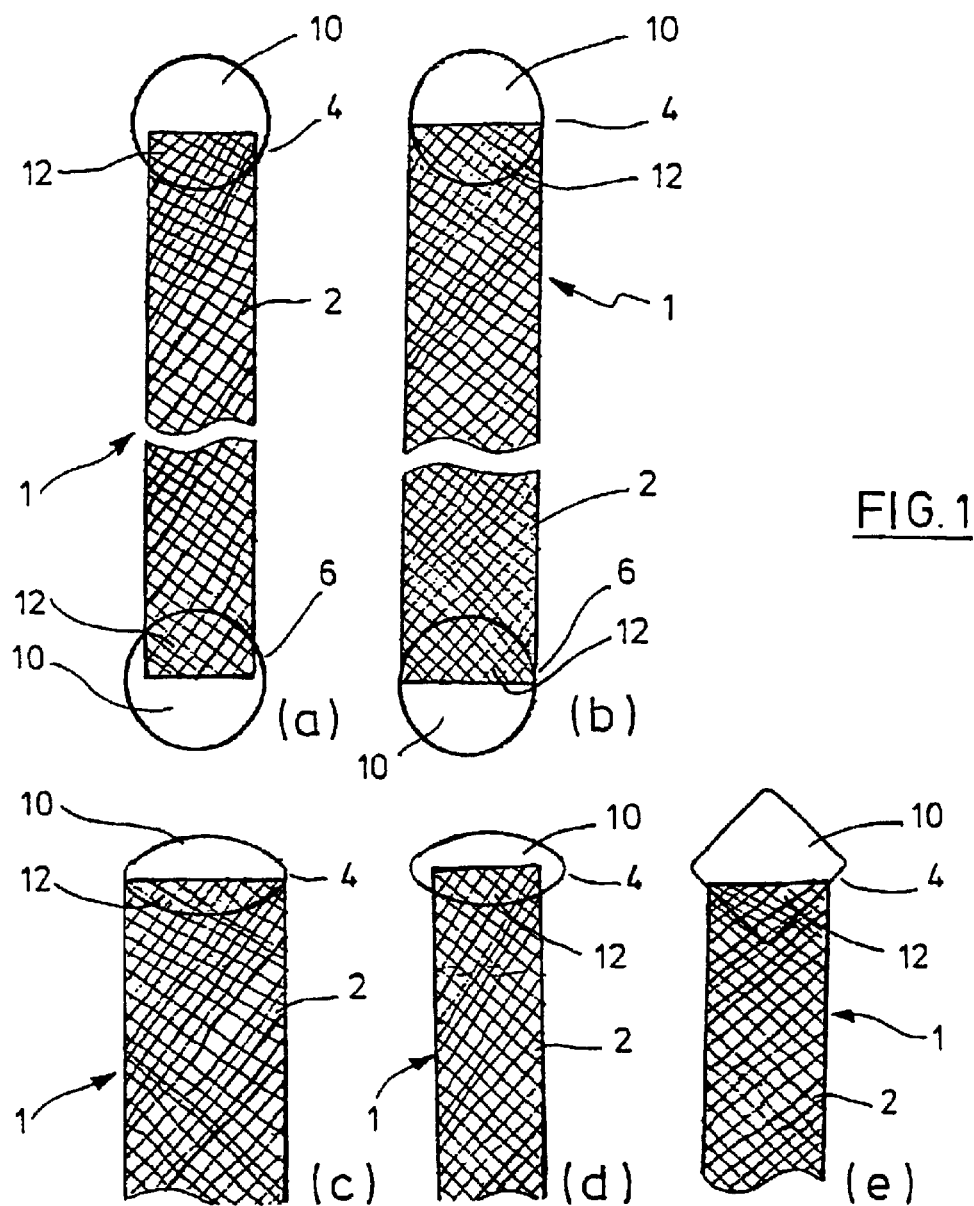
Figure 2:
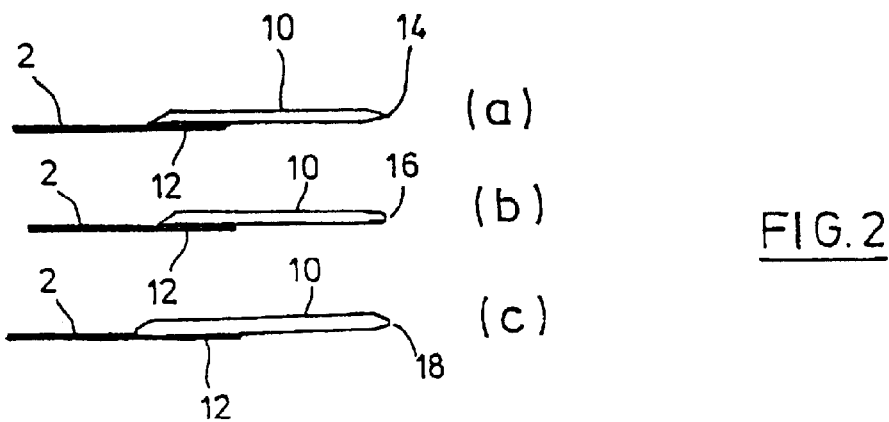

In FIGS. 1 and 2, various versions of a strip-like implant 1 are shown in which, for simplicity's sake, the same reference numbers are used for similar parts.

Each of the strip-like implants 1 has a tape 2 with a first end 4 and a second end 6. The tape 2 is a conventional mesh strip of implantable material and can be resorbable or non-resorbable.

In the area of the first end 4 of the tape 2, in all cases, a disk-like application aid in the form of a one-piece disk 10 is attached on the upper side of the tape 2 in an end zone 12, as can be seen in particular in FIG. 2. The versions according to FIG. 1(a) and FIG. 1(b) are in addition provided with a corresponding small disk 10 in the area of the second end 6 of the tape 2. In principle, a disk-like application aid can be attached in the area of one or in the area of both ends of the tape 2.

In the embodiments according to FIGS. 1 and 2, the small disk 10 is stuck or clipped onto the tape 2 in the end zone 12. Combinations of these means of attachment or other means of attachment, such as e.g. melting on, are also conceivable. The small disk 10 consists preferably of metal, plastic or ceramic.

The versions of the strip-like implant 1 differ in the design of the small disk 10. In FIG. 1(a), the small disk 10 has a circular outline and a somewhat greater diameter than the width of the tape 2. In the version according to FIG. 1(b), the diameter of the small disk 10 corresponds to the width of the tape 2. FIG. 1(c) shows a small disk 10 with an elliptical outline, the greatest expanse of which is aligned with the width of the tape 2 and is the same as the width. In the version according to FIG. 1(d), the small disk 10 is shaped and aligned similarly, but wider than the tape 2. FIG. 1(e) shows a rhombic small disk 10 which is somewhat wider than the tape 2.

As can be seen in FIG. 2, the small disks 10 are aligned with the plane of the tape 2 and relatively flat. In FIG. 2(a), a version is shown with a small disk 10, the front edge 14 of which is constructed as a cutting edge. In the version according to FIG. 2(b), the front edge 16 of the small disk 10 is blunt and atraumatic whilst the shape of the front edge 18 in FIG. 2(c) is in between.

Figure 3:
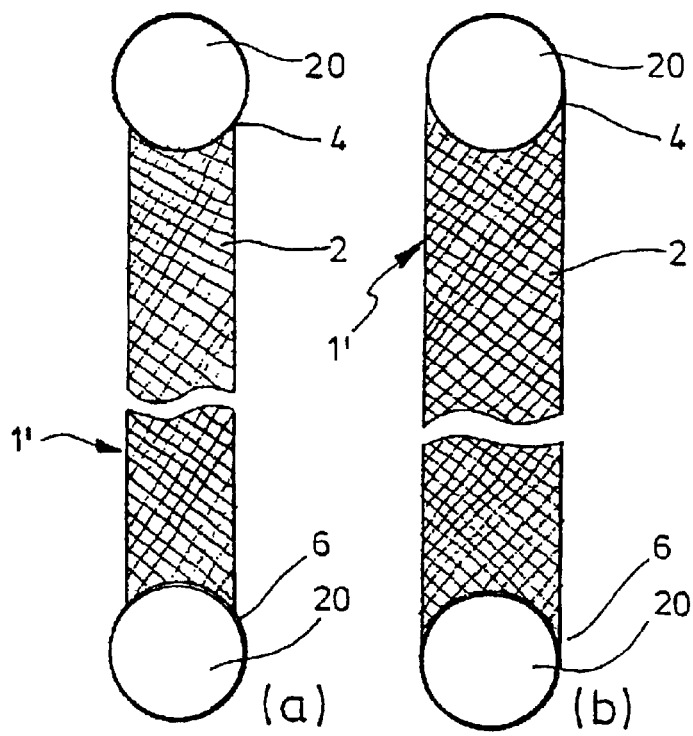
Figure 4:
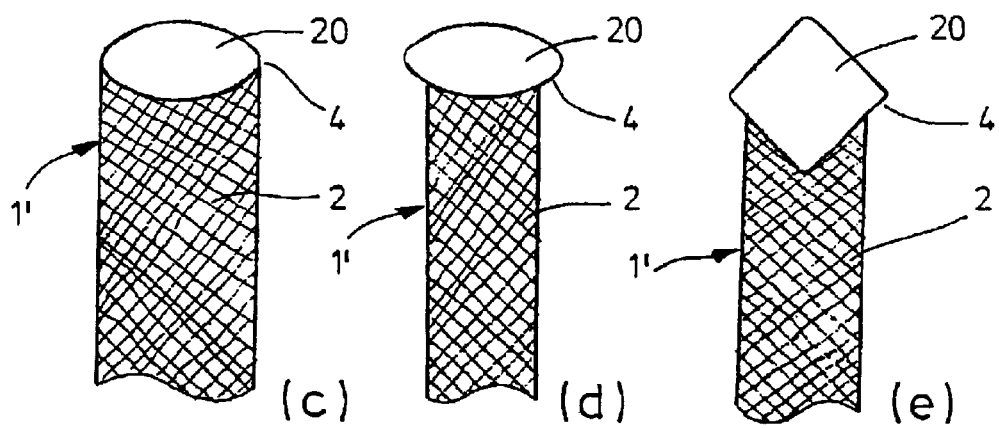
Figure 4:
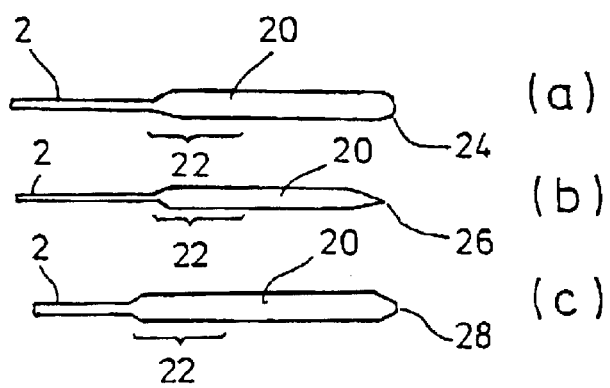

In FIGS. 3 and 4, further versions for strip-like implants are shown, each here numbered 1'. Otherwise, for simplicity's sake, the same reference numbers are used for similar parts, which, when possible, are the same as those from FIGS. 1 and 2.

The versions according to FIGS. 3 and 4 differ from the versions according to FIGS. 1 and 2 in the design of the disk-like application aid here numbered 20. The application aid 20 encloses an end zone 22 of the tape 2 as indicated in FIG. 4. There are different possible ways of achieving this. Thus, the application aid 20 can be constructed as a double disk, the two parts of which are attached on opposite sides of the tape 2 and enclose the tape between them. A recess to house the end zone 22 of the tape 2 can be provided on the insides of the disks so that the application aid 20 can have a smooth edge as indicated in FIG. 4. It is also conceivable to pour the material for the application aid 20 round the end zone 22 in the area of the first end 4 or the second end 6 of the tape 2, to fully shape the application aid and then carry out a curing (e.g. by cooling from the melt or by chemical reaction).

The versions according to FIGS. 3 and 4 differ in the design of the application aid 20. Its shape is circular in FIG. 3(a) (the diameter being greater than the width of the tape 2), circular in FIG. 3(b) (the diameter being the same as the width of the tape 2), elliptical in FIG. 3(c) and FIG. 3(d) (the application aid 20 being wider in FIG. 3(d) than the tape 2) and rhombic in FIG. 3(e).

FIG. 4 shows that in these versions the application aid 20 is arranged essentially symmetrical to the plane of the tape 2 and is flat overall. FIG. 4(a) shows a version with an atraumatically shaped front edge 24, FIG. 4(b) a version with a cutting front edge 26 and FIG. 4(c) a version with a front edge 28, the shape of which lies between these two extremes.

In order to insert one of the strip-like implants 1 or 1' into tissue, the application aid 10 or 20 is gripped with a surgical gripping instrument such as e.g. a forceps and pressed against one side of the tissue so that the front edge of the small disk 10 or of the application aid 20 (e.g. the edge 14) comes to lie freely against this side of the tissue. The small disk 10 or the application aid 20 can then be pressed through the tissue using the gripping instrument and, as soon as a part of it has emerged on the other side of the tissue, be pulled through the tissue by gripping this part with the gripping instrument, the tape 2 following. The opening created in the tissue in this way causes the patient little discomfort as it is matched well to the size of the tape 2. After the tape 2 is guided through the tissue, the small disk 10 or the application aid 20 can be cut off. Afterwards, the procedure with the tape 2 is as per usual for the operating technique concerned.

Alternatively, sharp-pointed forceps can be used as a gripping instrument, these being pushed through the tissue in order to grip the application aid 10 or 20 moved to the other side of the tissue. Subsequently, using the forceps, the application aid 10 or 20 and the following tape 2 are pulled through the tissue. In this way, the forceps initially ensure a small opening in the tissue, this then being increased by the application aid 10 or 20 to the size required for pulling through the tape 2.

Figure 5:
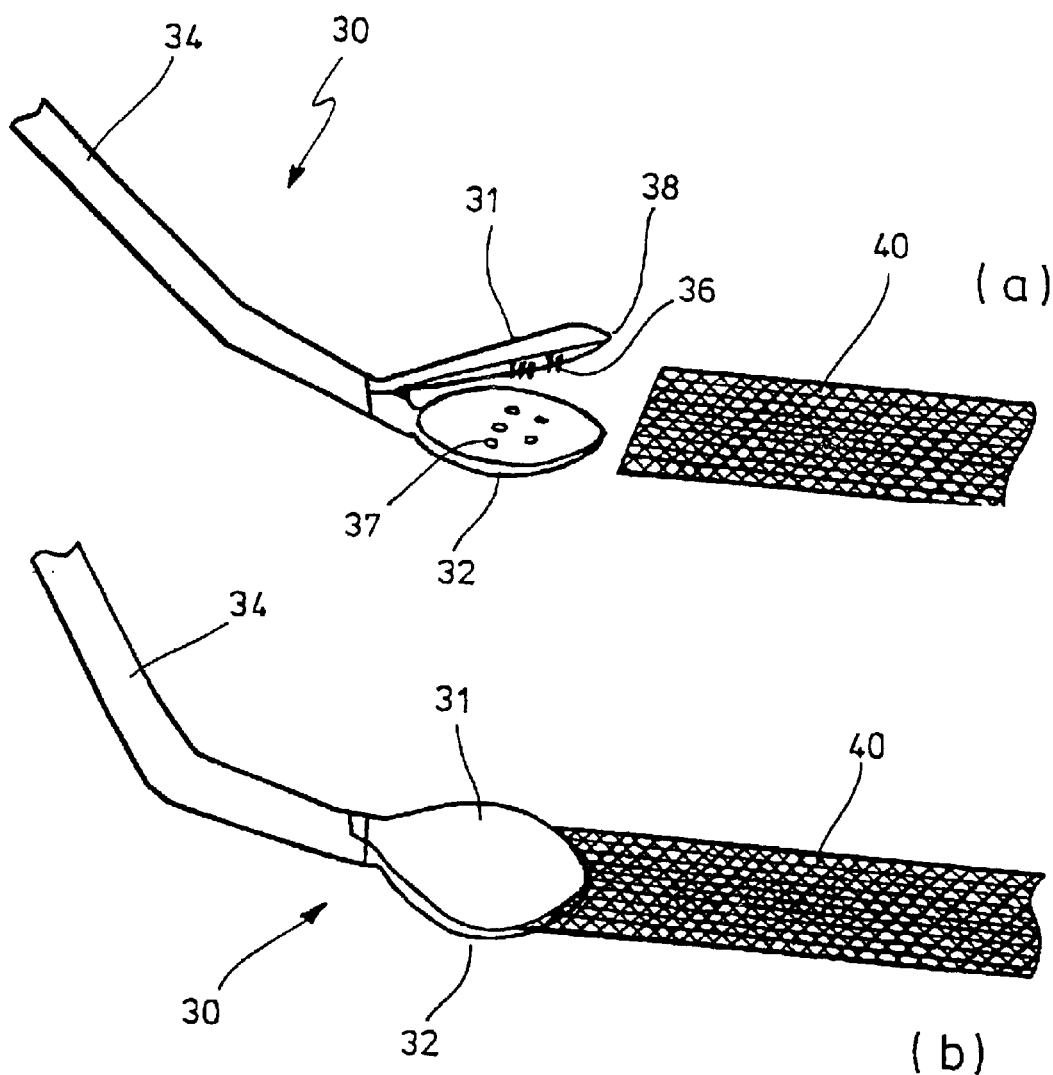

In FIG. 5, another possibility for an application aid is shown. The distal area of a surgical gripping instrument 30 with a first jaw 31 and a second jaw 32 is shown in perspective view, in FIG. 5(*a*) with opened jaws 31, 32 and in FIG. 5(*b*) with closed jaws 31, 32. The two jaws 31, 32 are connected to each other in articulated manner at the distal end of a shaft 34 and can be swivelled against each other via a mechanism not shown in more detail and guided in the shaft 34.

The jaws 31, 32 are designed so that they form a disk-like application aid when closed, thus e.g. have a similar overall shape to the small disks 10 according to FIGS. 1 and 2 or the application aids 20 according to FIGS. 3 and 4. The surgical gripping instrument 30 is set up to grip an implant tape, for which reason the insides of the jaws 31, 32 are preferably generally flat, but provided with clamping means in order to prevent the implant tape from slipping out. On the inside of the first jaw 31, the version of the surgical gripping instrument 30 shown in FIG. 5 has a plurality of spikes 36 opposite which, in the second jaw 32, recesses 37 are arranged, in which the spikes 36 engage when the jaws 31, 32 are closed. In the embodiment, both the front edge 38 of the first jaw 31 and its side edges are cutting edges. The edges of the second jaw 32 are designed correspondingly.

FIG. 5(*a*) shows the surgical gripping instrument 30 with opened jaws 31, 32 opposite the end area of a conventional implant tape 40. In the position shown in FIG. 5(*b*), the implant tape 40 is clamped between the jaws 31, 32, the shaft 34 running as an extension of the implant tape 40. In this way, it is possible to pull the implant tape 40 or also to pull it through tissue after the end zone of the implant tape 40 has already passed through the tissue. On the other hand, to create an opening for the implant tape 40 in the tissue, the surgical gripping instrument 30 must be applied differently, i.e. rotated by approximately 180°. Then the front edge 38 points towards the tissue and the closed jaws 31, 32 as well as the following implant tape 40 can be pressed through the tissue, in a similar way to that described previously in connection with FIGS. 1 to 4. Alternatively, the gripping instrument 30 can be used with closed jaws 31, 32 (and without the implant tape 40) in order to create an opening at the desired position in the tissue. Subsequently, the closed jaws 31, 32 are pushed through this opening in order to be able to grip the implant tape 40 moved to the opposite side of the tissue and to pull it through the opening in the configuration according to FIG. 5(*b*).

What is claimed is:

1. A strip-like implant for implantation in tissue during a surgical operation, the implant comprising:

a substantially flat, flexible mesh tape having a first end and a second end and a porous outer surface for binding the tape to the tissue when implanted; and first and second application aids affixed to and extending outwardly from the first and second ends of the mesh tape respectively, the first and second application aids being composed of a material different from the mesh tape and enabling the tape to be pulled through the tissue, the application aids lying in substantially the same plane as the first and second ends respectively, and having a maximum cross-section at least as large as the cross-section of the first and second ends of the tape respectively, the first and second application aids further having a tissue penetrating leading edge.

2. The implant according to claim 1, wherein the first and second application aids are disc elements affixed to one side of the tape.

3. The implant according to claim 1, wherein the first and second application aids further comprise first and second disc elements, the first disc elements being affixed to a first side of the tape and the second disc elements being affixed to a second side of the tape.

4. The implant according to claim according to claim 1, wherein the first and second application aids are affixed to the tape by clipping, gluing, welding, casting around, or melting-on.

5. The implant according to claim 1, wherein the first and second application aids have a shape in the plane of the tape that is circular, elliptical, oval or rhombic.

6. The implant according to claim 1, wherein the leading edge of the first and second application aids are atraumatic.

7. The implant according to claim 1, wherein the leading edge of the first and second application aids is a cutting edge.

* * * * *